(12) United States Patent
Park et al.

(10) Patent No.: US 8,728,775 B2
(45) Date of Patent: May 20, 2014

(54) METHOD FOR PREPARING 2-PYRROLIDONE USING A MICROORGANISM CONTAINING GLUTAMATE DECARBOXYLASE

(75) Inventors: Dong Cheol Park, Suwon-si (KR); Ki Kueon Kang, Icheon-si (KR); Hyun Jung Park, Seoul (KR); Seo Hyoung Kim, Busan (KR); Jae Young Oh, Yongin-si (KR)

(73) Assignee: Daesang Corporation, Seoul (KR)

( * ) Notice: Subject to any disclaimer, the term of this patent is extended or adjusted under 35 U.S.C. 154(b) by 0 days.

(21) Appl. No.: 13/876,926

(22) PCT Filed: Sep. 30, 2011

(86) PCT No.: PCT/KR2011/007268
§ 371 (c)(1),
(2), (4) Date: Mar. 29, 2013

(87) PCT Pub. No.: WO2012/044120
PCT Pub. Date: Apr. 5, 2012

(65) Prior Publication Data
US 2013/0203131 A1    Aug. 8, 2013

(30) Foreign Application Priority Data

Sep. 30, 2010 (KR) .................. 10-2010-0095515
Feb. 21, 2011 (KR) .................. 10-2011-0015081
Feb. 21, 2011 (KR) .................. 10-2011-0015085
May  4, 2011 (KR) .................. 10-2011-0042255

(51) Int. Cl.
*C12P 17/10* (2006.01)

(52) U.S. Cl.
USPC ........................................................ 435/121

(58) Field of Classification Search
USPC ........................................................ 435/121
See application file for complete search history.

(56) References Cited

FOREIGN PATENT DOCUMENTS

| JP | 2002-121183 | 4/2002 |
| JP | 2009-159840 | 7/2009 |
| KR | 1020090128767 A | 12/2009 |

OTHER PUBLICATIONS

Pennacchietti E. et al. Mutation of His465 Alters the pH Dependent Spectroscopic Properties of *E. coli* Glutamate Decarboxylase . . . J Biol Chem 284(46)31587-96, Nov. 13, 2009.*
Strausbauch P. et al. Chemical and Physical Properties of *E. coli* Glutamate Decarboxylase. Biochemistry 9(2)226-233, Jan. 20, 1970.*
International Search Report for PCT/KR2011/007268, mailed May 30, 2012 (2 pages).

* cited by examiner

*Primary Examiner* — Ralph Gitomer
(74) *Attorney, Agent, or Firm* — Clark & Elbing LLP (57) ABSTRACT

The present invention relates to a method for preparing 2-pyrrolidone using biomass, comprising: a step (a) of culturing a microorganism which contains glutamate decarboxylase as a whole-cell catalyst in a culture medium containing glutamic acid or glutamate so as to prepare 4-amino butyric acid; a step (b) of filtering the 4-amino butyric acid from the culture medium in order to obtain the 4-amino butyric acid; and a step (c) of converting the 4-amino butyric acid into 2-pyrrolidone. The present invention provides a series of processes for preparing 2-pyrrolidone from glutamic acid or glutamate using biomass. According to the present invention, 4-amino butyric acid is prepared using a microorganism as a whole cell, and preferably, 4-amino butyric acid which has not undergone a complicated refining process such as a crystallization process is directly used to prepare 2-pyrrolidone at a high yield rate in an economically advantageous manner. According to the present invention, 2-pyrrolidone may be mass-produced at a high yield rate and low production costs. The method of the present invention simplifies processes for preparing 2-pyrrolidone, and thus is suitable for mass production at an industrial scale.

17 Claims, 2 Drawing Sheets

METHOD FOR PREPARING 2-PYRROLIDONE USING A MICROORGANISM CONTAINING GLUTAMATE DECARBOXYLASE

CROSS-REFERENCE TO RELATED APPLICATIONS

This application is the U.S. national stage filing under 35 U.S.C. §371 of International Application No. PCT/KR2011/007268, filed Sep. 30, 2011, which claims priority from Korean Patent Applications 10-2010-0095515, filed Sep. 30, 2010, 10-2011-0015081, filed Feb. 21, 2011, 10-2011-0015085, filed Feb. 21, 2011, and 10-2011-0042255, filed May 4, 2011.

FIELD OF THE INVENTION

The present invention relates to a method for preparing 2-pyrrolidone. More specifically, the present invention relates to a method for preparing 2-pyrrolidone from glutamic acid or glutamate using a biomass.

DESCRIPTION OF THE RELATED ART 2-pyrrolidone is a useful chemical substance used as industrial materials in a variety of fields such as manufactures of polymer, solvents for chemical reactions and specialty inks.

A representative method known to manufacture 2-pyrrolidone is disclosed in BASF's patent application (WO 03/022811) in which gamma-butyrolactone as petrochemicals is continuously prepared using ammonia in liquid phase under high-temperature and high-pressure reaction conditions. In addition, there are known methods that 2-pyrrolidone is prepared by using succinic acid or succinic anhydride as starting materials (U.S. Pat. No. 4,904,804), or by using maleic acid or succinonitrile as starting materials (U.S. Pat. Nos. 4,325,872, 4,193,925, 4,181,662 and 4,123,438). However, the raw materials used in these methods are crude oil-dependent and therefore their price is significantly fluctuated. In addition, their price is likely to continuously increase due to insufficiency of oil resources.

Under these circumstances, recent researches to obtain chemicals from low-cost biomasses have been actively made. For instance, there are well known processes in which glutamic acid is obtained from biomass by fermentation and then converted to 4-aminobutyric acid (or GABA) by an enzymatic reaction, one of amino acids as health functional food material. In addition, several methods for preparing 2-pyrrolidone from 4-aminobutyric acid have been reported.

The approach for preparing 2-pyrrolidone from 4-aminobutyric acid has been reported by Pathak, et al. (*Tetrahedron* 46(5):1733-1744 (1990)), in which an intermediate process for synthesizing precursors of carcinogens is executed in toluene as reaction solvents in the presence of 4-aminobutyric acid and excess of neutral alumina for approximately 10 hours at reflux temperature for synthesizing 2-pyrrolidone. The Korea Research Institute of Chemical Technology has suggested another process in which 2-pyrrolidone is prepared in toluene by adding a catalyst or dehydrating agent to 4-aminobutyric acid in accordance with processes reported by Pathak, et al. (Korean Patent Application Publication No. 2009-0128767). However, these methods have disadvantages including requirement for additional filtration process for catalyst removal, cost for additional raw materials and purification of 2-pyrrolidone from reaction solvents.

Meanwhile, Japanese Patent Application Publication No. 2002-121183 suggests a method for manufacturing 2-pyrrolidone by reacting 4-aminobutyric acid and water in high-temperature (200-300° C.) and high-pressure water (15-30 megapascal). However, this method also has shortcomings due to its high-temperature and high-pressure reaction conditions, including increase in utility costs and requirement for huge equipment investments in mass production. Japanese Patent Application Publication No. 2009-159840 discloses various reaction solvent conditions for manufacturing pyrrolidone using 4-aminobutyric acid. Particularly, the method suggests that pyrrolidone mixed with 4-aminobutyric acid may allow reaction temperatures to be decreased, suggesting a preferable reaction temperature, 180° C. However, this method presents no solutions to problems such as higher cost due to high reaction temperatures and process operation difficulties caused by water (vapor) generated explosively at the high reaction temperature, 180° C., which becomes more serious in mass production.

Even though 4-aminobutyric acid is known to be degraded to 2-pyrrolidone and water at the melting point temperature (202° C.) (Merck index 430), it may be tremendously difficult to generate 2-pyrrolidone and water by dissolving at the melting point temperature (202° C.) with stirring a large amount of 4-aminobutyric acid at one time for mass production. Moreover, there are considerable difficulties in process operations, for example, a large amount of water (water vapor) explosively generated at this time causing overflow troubles of reaction liquids.

Meanwhile, there are no prior arts describing a whole process to prepare pyrrolidone from glutamic acid or glutamate as starting materials using biomass. Under such circumstances, it would be recognized that efficient processes for preparing pyrrolidone from glutamic acid or glutamate using biomass may greatly improve cost-effectiveness in the production field of pyrrolidone.

Throughout this application, various patents and publications are referenced and citations are provided in parentheses. The disclosure of these patents and publications in their entireties are hereby incorporated by references into this application in order to more fully describe this invention and the state of the art to which this invention pertains.

DETAILED DESCRIPTION OF THIS INVENTION

Technical Purposes of This Invention

The present inventors have made intensive researches to develop a method for preparing 2-pyrrolidone at a high yield rate and low production costs. As a result, they have developed process protocols that 2-pyrrolidone may be mass-produced at a high yield rate and low production costs from glutamic acid or glutamate using directly a biomass.

Accordingly, it is an object of this invention to provide a method for preparing 2-pyrrolidone.

Other objects and advantages of the present invention will become apparent from the detailed description to follow taken in conjugation with the appended claims and drawings.

Technical Solutions of This Invention

In one aspect of the present invention, there is provided a method for preparing 2-pyrrolidone, comprising the steps of:

(a) preparing 4-aminobutyric acid by culturing a microorganism as a whole-cell catalyst which contains glutamate decarboxylase in a culture medium containing glutamic acid or glutamate;

(b) obtaining 4-aminobutyric acid by filtering the culture medium; and (c) converting 4-aminobutyric acid to 2-pyrrolidone.

The present inventors have made intensive researches to develop a method for preparing 2-pyrrolidone at a high yield rate and low production costs. As a result, they have developed process protocols that 2-pyrrolidone may be mass-produced at a high yield rate and low production costs from glutamic acid or glutamate using directly a biomass.

Each stage of the present method will be described in detail as follows:

Step (a): Preparation of 4-Aminobutyric Acid Using a Biomass

According to the present invention, the present invention prepares 4-aminobutyric acid using a microorganism itself as a whole-cell catalyst without destruction of the microorganism.

The microorganism as a whole-cell catalyst may be used any of microorganisms which are not available physical/chemical modifications.

Preferably, the microorganism containing glutamate decarboxylase used as a whole-cell catalyst in the present invention is pre-treated with an organic solvent (preferably, a hydrophobic organic solvent) in order to selective permeability of cell membrane.

The microorganism used in the present invention contains glutamate decarboxylase and the present invention may be preferably used the microorganisms of *Aspergillus* spp., *Clostridium* spp., *Escherichia* spp., *Lactobacillus* spp., *Lactococcus* spp. or *Listeria* spp., more preferably *Escherichia* spp., *Lactobacillus* spp. or *Lactococcus* spp., and most preferably *Escherichia coli*.

The present invention may be used the microorganisms of *Aspergillus* spp., preferably *Aspergillus aculeatus*, *Aspergillus caesiellus*, *Aspergillus candidus*, *Aspergillus carneus*, *Aspergillus clavatus*, *Aspergillus deflectus*, *Aspergillus fischerianus*, *Aspergillus flavus*, *Aspergillus oryzae*, *Aspergillus fumigatus*, *Aspergillus glaucus*, *Aspergillus nidulans*, *Aspergillus niger* or *Aspergillus ochraceus*, more preferably *Aspergillus fischenanus*, *Aspergillus flavus* or *Aspergillus oryzae*, most preferably *Aspergillus oryzae*.

The present invention may be used the microorganisms of *Clostridium* spp., preferably *C. acetobutylicum*, *C. aerotolerans*, *C. baratii*, *C. beijerinckii*, *C. bifermentans*, *Clostridium perfingens*, *C. botulinum*, *C, butyricum*, *C. cadaveris*, *C. chauvoei*, *C. clostridioforme*, *C. colicanis*, *C. difficile*, *C. estertheticum*, *C. fallax* or *C. feseri*, more preferably *C. beijerinckii*, *C. bifermentans*, *Clostridium perfingens* or *C. botulinum*, most preferably *Clostridium perfingens*.

The present invention may be used the microorganisms of *Lactobacillus* spp., preferably *E. albertii*, *E. blattae*, *E. coli*, *E. fergusonii*, *E. hermannii* or *E. vulneris*, more preferably *E. blattae*, *E. coli* or *E. fergusonii*, most preferably *E. coli*. The present invention may a general *E. coli* strain, preferably genetically engineered *E. coli* which is allowed to over-express glutamate decarboxylase.

The present invention may be used the microorganisms of *Lactobacillus* spp., preferably *L. acetotolerans*, *L. acidifarinae*, *L. acidipiscis*, *L. acidophilus*, *L. agilis*, *L. algidus*, *L. alimentarius*, *L. amylolyticus*, *L. amylophilus*, *L. composti*, *L. crustorum*, *L. dextrinicus*, *L. dioliivorans*, *L. equigenerosi*, *L. fermentum*, *L. gallinarum*, *L. ghanensis*, *L. hilgardii*, *L. iners*, *L. johnsonii*, *L. leichmannii*, *L. nagelii*, *L. helveticus*, *L. brevis*, *L. buchneri*, *Lactobacillus lactis*, *L. casei*, *L. kimchii*, *L. plantarum*, *L. reuteri*, *L. sanfranciscensis* or *L. sakei*, more preferably *L. brevis*, *L. buchneri*, *Lactobacillus lactis* or *L. casei*, most preferably *Lactobacillus lactis*.

The present invention may be used the microorganisms of *Lactobacillus* spp., preferably *L. garvieae*, *L. lactis*, *L. piscium*, *L. plantarum* or *L. raffinolctis*, more preferably *L. lactis* or *L. piscium*, most preferably *L. lactis*.

The present invention may be used the microorganisms of *Lactobacillus* spp., preferably *L. grayi*, *L. innocua*, *L. ivanovii*, *L. monocytogenes*, *L. seeligeri*, *L. muttayi* or *L. welshimeri*, more preferably *L. ivanovii* or *L. monocytogenes*, most preferably *L. monocytogenes*.

The selective permeability of microorganisms refers to a transportation between inside and outside in cells which is affected by environmental factors for water-soluble substrates of lipid bilayer constituting microorganism cell membrane. Although cell membranes have semipermeability not permitting to penetrate water-soluble molecules with high-molecular weights, lipid-soluble molecules are likely to easily penetrate into cells by dissolving into the lipid portion of cell membranes, irrespectively of their molecular weights.

Where the cell membrane reacts with a hydrophobic organic solvent, the semipermeable membrane is destroyed such that the selective permeability in cell is diminished.

The types and concentrations of the hydrophobic organic solvents incubated with microorganisms in the present invention are considerable factors in the senses that they enable to destroy the selective permeability of microorganisms, elevate the intracellular content of 2-aminobutyric acid and reuse whole-cell catalysts.

The present invention may be used hydrophobic organic solvents which are reacted to microorganisms to destroy the selective permeability, preferably Pentanes, Hexane, Decane, Cyclohexane, Cyclopentane, 1-Butylene, 2-Butylene), 1-Pentene, 2-Pentene, Isobutylene, Carbon tetrachloride, 1-Chlorobutane, 1-Chloropentane, 2-Chloropropane, 1-Chloropropane, Bromoethane, Chloroform, Dichloromethane, 1-Nitropropane, Nitromethane, Benzene, Toluene, Xylene, Chlorobenzene, Aniline, Diethyl ether, Diisopropyl ether, Tetrahydrofuran, Ethyl acetate, Methyl acetate, Carbon disulfide, Diethyl sulfide, Dimethyl sulfoxide, Diethylamine, Acetonitrile, Pyridine, more preferably Toluene, Chloroform, Xylene, Cyclohexane, and most preferably Toluene.

In the present invention, the concentration of the hydrophobic organic solvent is preferably 0.01-20% (v/v), more preferably 0.1-1% (v/v), and most preferably 0.2-0.5% (v/v).

The term '(v/v)' denotes the volume of a hydrophobic organic solvent/the volume of a microorganism suspension. Where more than 20% (v/v) of the organic solvent is used, the catalyst activity may be inhibited and the recovery of bacterial cells may become problematic. In case of using less than 0.01% (v/v) of the organic solvent, the selective permeability of cell membranes is unlikely to be sufficiently destructed.

The microorganism containing glutamate decarboxylase and the hydrophobic organic solvent are stirred to pre-treat. The stirring rate is preferably 100-600 rpm, more preferably 200-400 rpm, and most preferably 200-300 rpm.

The stirring time is preferably 1-60 min, more preferably 3-30 min, and most preferably 5-15 min.

In addition, the stirring temperature is preferably 4-40° C., more preferably 15-35° C., and most preferably 25-30° C.

According to a preferred embodiment, after preparation of the whole-cell catalyst by the processes, the present method further comprises the step of suspending the whole-cell catalyst in water or a buffer. The pH of glutamate decarboxylase having its catalytic activity ranges from 3.5 to 6.0. Where the pH is out of the range, the activity is sharply dropped. In the process of converting glutamic acid to gamma-aminobutyric acid by glutamate decarboxylase, protons in the aqueous solution are consumed to increase pH. Therefore, the pH needs to be adjusted.

More specifically, based on the fact that pKa value of glutamic acid used in the present invention is 2.2, the initial pH is adjusted not to be less than 3.5 using a buffer, while glutamate in excess amounts over its solubility is added to the aqueous solution of whole-cell catalyst.

The pH of the buffer used in the present invention is preferably pH 3.8-8.0, more preferably pH 4.0-7.0, and still more preferably pH 4.0-6.0. The buffer with pH 4.5 was prepared with acetic acid, and the buffers with pH 6.0, 7.0 or 8.0 were prepared with phosphoric acid, but not limited to.

Meanwhile, where glutamic acid is used as a substrate, the pH of the buffer used in the present invention is preferably pH 4.0-8.0, more preferably pH 4.5-7.0, still more preferably pH 5.0-6.0, and most preferably 6.0. Where sodium glutamate is used as a substrate in the step (b), the pH of the buffer used in the present invention is preferably pH 3.8-6.5, more preferably pH 3.8-6.0, still more preferably pH 3.8-5.5, still further more preferably pH 3.8-5.0 and most preferably 4.0.

According to the present invention, glutamic acid or glutamate (preferably, sodium glutamate) is converted to 4-aminobutyric acid by a whole-cell catalyst.

The glutamic acid used in the present invention is one of 20 amino acids. The sodium glutamate has the molecular formula of $HOOC(CH_2)_2CH(NH2)COONa$ and the molecular weight of 169.11. It is the sodium salt of glutamic acid.

The most important feature of the present invention is to available of glutamic acid, in addition to use of sodium glutamate, for preparing 4-aminobutyric acid. Glutamic acid is cheaper than sodium glutamate in price. Therefore, gamma-aminobutyric acid is prepared using glutamic acid, whereby the unit price of the product may be reduced.

The concentration of whole-cell catalyst is adjusted depending on the amount of glutamate decarboxylase which is contained in the whole-cell catalyst. According to a preferred embodiment, in case of *E. coli*, normal strain which is non-subjected to any of artificial genetic manipulations is used. The concentration of the normal strain is preferably 1-30 g/L of strain, more preferably 5-20 g/L of strain, and most preferably 10-15 g/L of strain. In addition, genetically engineered strain which is allowed to massively produce glutamate decarboxylase is used. The concentration of the genetically engineered strain is preferably 1-30 g/L of strain, more preferably 1-10 g/L of strain, and most preferably 1-5 g/L of strain.

Glutamic acid or sodium glutamate reacted with whole-cell catalyst is biologically prepared from a biomass. They may be introduced into a reactor containing whole-cell catalyst along with a powder form or an aqueous solution form. The amount of glutamic acid or sodium glutamate is added in the amount of wt % based on the weight of suspension of microorganism, preferably 15-55 wt %, more preferably 30-50 wt %, and most preferably 35-45 wt %. Where the amount is less than 15 wt %, the concentration of the generated gamma-aminobutyric acid is low such that its industrial value is depreciated in terms of concentration costs. Where the amount is higher than 55 wt %, the agitation is troublesome and the conversion rate is decreased to below 90%. Glutamic acid or sodium glutamate may be introduced with a powder form or a suspension form. It is unnecessary to dissolve all glutamic acid.

According to a preferred embodiment, the reaction of whole-cell catalyst and glutamic acid or sodium glutamate may further comprise pyridoxal 5-phosphate (PLP) to proceed the reaction. Pyridoxal 5-phosphate is one of coenzymes which act to various enzymatic reactions in vivo such as racemization of amino acids, transamination, decarboxylation, dehydrogenation, dealdehydation, synthesis of tryptophan from serine and indole. It plays a role to accelerate the reaction Step (b): Filtration of Culture Medium After preparation of 4-aminobutyric acid using the whole-cell catalyst and the medium containing glutamic acid or glutamate as a substrate, the medium is filtered to isolate 4-aminobutyric acid from bacterial cells and insoluble components in the medium.

The filtration is to remove bacterial cells and insoluble components from the medium. The filtration may perform using various methods known in the art, for example, centrifugation, filter press, membrane filter and filter paper.

According to a preferred embodiment, between the steps (a) and (b), the method further comprises the step of removing a pigment in the culture media by treating the culture media with an activated carbon.

A treatment of an activated carbon may perform using various methods known in the art and there are two ways, method to treat activated carbons directly to the medium and method to use a column packed with activated carbons.

Considering both of production costs and processes conveniences, the method to treat activated carbons directly to the medium is more suitable for the present invention.

According to the method to treat activated carbons directly to the medium, the activated carbon is added in the amount of 1-10 wt % based on the weight of 4-aminobutyric acid in the culture media, preferably 1.5-4.0 wt %, and more preferably 2.0-4.0 wt %. As shown in Example, there are problems. Where the treatment amount of activated carbons is higher than 4.0 wt %, the loss rate of 4-aminobutyric acid is increased such that the recovery efficiency of 2-pyrrolidone is finally decreased. Where the treatment amount of activated carbons is less than 1.5 wt %, impure pigments are not sufficiently removed such that the recovery efficiency of 2-pyrrolidone is decreased.

Alternatively, the treatment of activated carbons may perform using the column packed activated carbons. For instance, The medium is loaded to the column packed activated carbons and the eluant is obtained from the column, whereby the 4-aminobutyric acid solution removed impure pigments may be collected. When the column uses, the removal of pigments and filtration of the medium may be simultaneously achieved.

According to a preferred embodiment, the resultant of the step (a) is centrifuged to isolate bacterial cells and the isolated solution is treated with activated carbons to remove pigments such that the present invention obtains 4-aminobutyric acid. Preferably, before the treatment of activated carbons, the medium in which bacterial cells are isolated is heat-treated.

According to a preferred embodiment, the solution containing 4-aminobutyric acid obtained through filtration is concentrated to use synthesis of 2-pyrrolidone.

According to a preferred embodiment, after the step (b), the method further comprises the step of isolating the whole-cell catalyst and reusing the isolated whole-cell catalyst. Since the present method uses a microorganism itself without destruction of the microorganism, the present method may reuse the microorganism containing glutamate decarboxylase by centrifugation in which the microorganism is easily collected. The step (b) may be repeated using the collected microorganism. In addition, 4-aminobutyric acid may be also prepared by further introducing the collected microorganism into the reactor in which the preparation reaction for 4-aminobutyric acid has been already executed.

Step (c): Preparation of 2-Pyrrolidone from 4-Aminobutyric Acid 2-pyrrolidone is prepared using 4-aminobutyric acid obtained in the process described as above.

According to a preferred embodiment, 4-aminobutyric acid used in the step (c) is non-pre-purified. The phrase "4-aminobutyric acid which is non-pre-purified" means crude 4-aminobutyric acid which is non-subjected to other purification processes (e.g., crystallization) besides the filtration and/or the treatment of activated carbons described as above.

Basically, the conversion of 4-aminobutyric acid to 2-pyrrolidone is a lactam cyclization reaction. Synthesizing 2-pyrrolidone using 4-aminobutyric acid may perform by various methods known in the art.

According to a preferred embodiment, the conversion of 4-aminobutyric acid to 2-pyrrolidone in the present method is first proposed by the present inventors and it is called a "DPSP" (Daesang Pyrrolidone Synthesis Protocol). The DPSP method is efficient and cost-effective method.

The DPSP basically includes the steps of:

(c-1) preparing a reaction composition in which 4-aminobutyric acid and 2-pyrrolidone are mixed;

(c-2) generating 2-pyrrolidone and water by heating the reaction composition for lactam cyclization reaction; and (c-3) isolating 2-pyrrolidone.

More specifically, the DPSP method has two methods: DPSP-T method focusing on the adjustment of the temperature in the basic process described as above and DPSP-P method focusing on the adjustment of the pressure.

According to a preferred embodiment, the DPSP-T method includes the steps of:

(a) preparing a reaction composition in which 4-aminobutyric acid and 2-s pyrrolidone are mixed;

(b) generating 2-pyrrolidone and water by heating the reaction composition for lactam cyclization reaction at 118° C.-148° C.; and (c) isolating 2-pyrrolidone.

According to a preferred embodiment, the DPSP-P method includes the steps of:

(a) preparing a reaction composition in which 4-aminobutyric acid and 2-pyrrolidone are mixed;

(b) generating 2-pyrrolidone and water by heating the reaction composition for lactam cyclization reaction and removing water; and (c) isolating 2-pyrrolidone.

The DPSP-T method will be described in detail as follows:

According to the DPSP-T method, in order to provide a suitable environment for the conversion reaction of 4-aminobutyric acid, a reaction composition in which 4-aminobutyric acid and 2-pyrrolidone are mixed is firstly prepared.

Where the reaction composition in which 4-aminobutyric acid and 2-pyrrolidone coexist is provided, 4-aminobutyric acid is converted to 2-pyrrolidone and water at lower temperature, for example, 118° C.-120° C., than the melting temperature of 4-aminobutyric acid, 202° C. as shown in Example.

The providing for reaction composition in which 4-aminobutyric acid and 2-pyrrolidone are mixed may be achieved by various methods.

First, the step (a) may be performed by stirring 4-aminobutyric acid and 2-pyrrolidone in the reactor. i.e., 4-aminobutyric acid and 2-pyrrolidone is fed into the reactor and stirred to prepare the reaction composition in which 4-aminobutyric acid and 2-pyrrolidone are mixed. This reaction composition may be subjected to lactam cyclization reaction at relatively low temperature, e.g., 118° C.-148° C.

The amount of 2-pyrrolidone mixed to 4-aminobutyric acid is not specifically limited. However, where the amount of 2-pyrrolidone mixed to 4-aminobutyric acid is very low, it results in problem to stir. In addition, where the amount of 2-pyrrolidone mixed to 4-aminobutyric acid is too much, it results in problem to increase costs for distillating 2-pyrrolidone after the reaction. Therefore, considering both convenience in process operation and preparation costs, the weight ratio of 4-aminobutyric acid to 2-pyrrolidone for the mixture amount is preferably 1:0.1-1:10, more preferably 1:0.2-1:5, and most preferably 1:0.5-1:2.

Second, the step (a) may be performed by feeding 4-aminobutyric acid into the reactor and elevating the temperature of the reactor to convert 4-aminobutyric acid to 2-pyrrolidone and water, followed by additionally feeding 4-aminobutyric acid into the reactor. For instance, 4-aminobutyric acid is fed into the reactor and the temperature of the reactor was elevated to convert 4-aminobutyric acid to 2-pyrrolidone and water. Afterwards, the reactor was naturally cooled and further added 4-aminobutyric acid to dissolve. If necessary, the additional addition of 4-aminobutyric acid may be performed into two doses.

Third, the step (a) may be performed by feeding 4-aminobutyric acid into the reactor and elevating the temperature of the reactor to convert partially 4-aminobutyric acid to 2-pyrrolidone and water. The difference from the second protocol described above is to use all the amount of 4-aminobutyric acid being converted to 2-pyrrolidone from in the initial step.

The reaction composition in which 4-aminobutyric acid and 2-pyrrolidone are mixed is provided by these processes regardless of choice for any of the three approaches described as above.

Afterwards, 2-pyrrolidone and water are generated by heating the reaction composition for lactam cyclization reaction at 118° C.-148° C.

When the reaction composition in the step (a) is maintained at an appropriate temperature, lactam cyclization reaction occurs such that 4-aminobutyric acid is converted to 2-pyrrolidone and water.

According to conventional techniques (for example, Japanese Patent Application Publication Nos. 2002-121183 and 2009-159840), 4-aminobutyric acid is converted to 2-pyrrolidone at the high temperature (e.g., 200-300° C. or 180° C.). The present invention produces 2-pyrrolidone and water by heating the reaction composition for lactam cyclization reaction at considerably lower temperature, i.e. 118-148° C., than temperatures as disclosed in the conventional techniques.

Where the reaction temperature is less than 118° C., the lactam cyclization reaction is little proceeded such that 2-pyrrolidone is little generated. Where the reaction temperature is higher than 148° C. (e.g., 200-300° C. or 180° C.), it results in problems such as process operation difficulties caused by water (vapor) generated explosively, which becomes more serious in mass production. The reaction temperature suggested by the present invention, 118° C.-148° C., does not require utilities for high temperature and/or high pressure while the conversion reaction is efficiently undertaken, thereby making the present invention be suitable for mass production.

Alternatively, the step (b) is performed under a reduced pressure condition such that water generated during the reaction may be removed. The reduced pressure condition in the present invention is preferably below 750 mmHg, more preferably below 120 mmHg, still more preferably 10-120 mmHg, still further more preferably 10-60 mmHg, and most preferably 20-60 mmHg.

Finally, 2-pyrrolidone is isolated from the reaction resultant of the step (b) and obtained with an appropriate purity and an appropriate yield.

The isolation of 2-pyrrolidone may be performed using various methods known in the arts. Preferably, the isolation of 2-pyrrolidone may be performed by distillation under reduced pressure. The distillation under reduced pressure for the isolation of 2-pyrrolidone is preferably 0.1-250 mmHg, more preferably 1-90 mmHg, still more preferably 1-50 mmHg, and still further more preferably 1-20 mmHg.

Finally, 2-pyrrolidone is obtained with high purity and high yield by the DPSP-T method in the present invention. Preferably, the present method shows a maximum yield of 99% and a maximum purity of 99.8% for 2-pyrrolidone, preferably yield of 90-99% and purity of 99.0-99.8%, more preferably yield of 96-99% and purity of 99.5-99.8%.

The DPSP-P method will be described in detail as follows:

According to the DPSP-P method, in order to provide a suitable environment for the conversion reaction of 4-aminobutyric acid, a reaction composition in which 4-aminobutyric acid and 2-pyrrolidone are mixed is firstly prepared. The preparing process for the reaction composition may be described with reference to that of the DPSP-T method.

Afterwards, 2-pyrrolidone and water are generated by heating the reaction composition for lactam cyclization reaction under reduced pressure conditions, and water is removed. When the reaction composition in the step (a) is maintained under reduced pressure conditions, lactam cyclization reaction occurs such that 4-aminobutyric acid is converted to 2-pyrrolidone and water, and water is removed from the reaction resultant.

One of the characteristics of DPSP-P processes is to remove water generated during the reaction by adding the reduced pressure condition in the conversion reaction of 4-aminobutyric acid. This removal of water may significantly increase the reaction, proceeded the reaction at lower temperature, and significantly enhanced the productivity for 2-pyrrolidone. The reduced pressure condition in the present invention is preferably below 750 mmHg, more preferably below 120 mmHg, still more preferably 10-120 mmHg, still further more preferably 10-60 mmHg, and most preferably 20-60 mmHg. The reaction temperature in the step (b) is preferably more than 110° C. (e.g., 110° C.-150° C.), more preferably more than 118° C., and still more preferably more than 118° C.-150° C.

Alternatively, the present invention shows an excellent yield and an excellent purity for 2-pyrrolidone even the temperature range of 118° C.-148° C. According to a preferred embodiment, 4-aminobutyric acid is converted to 2-pyrrolidone even at low temperature, e.g., 118° C. In the step (b), water is removed. According to a preferred embodiment, the removal of water in the step (b) is achieved simultaneously with performing the step (b). i.e., 4-aminobutyric acid is converted to 2-pyrrolidone and water, and water is immediately removed under reduced pressure condition. This removal of water is preferable to perform in a continuous manner. Alternatively, the removal of water in the step (b) is achieved in the middle of performing the step (b). Alternatively, the removal of water in the step (b) is achieved after performing the step (b).

Finally, 2-pyrrolidone is isolated from the reaction resultant of the step (b) and obtained with an appropriate purity and an appropriate yield. The isolation of 2-pyrrolidone may be described with reference to that of the DPSP-T method.

2-pyrrolidone is finally obtained with high purity and high yield by the DPSP-P method in the present invention. Preferably, the DPSP-P method in the present invention shows a maximum yield of 99% and a maximum purity of 99.8% for 2-pyrrolidone, preferably yield of 90-99% and purity of 99.0-99.8%, more preferably yield of 96-99% and purity of 99.5-99.8%.

Effects of This Invention

The features and advantages of this invention will be summarized as follows:

(a) The present invention provides a series of processes for preparing 2-pyrrolidone from glutamic acid or glutamate using biomass.

(b) According to the present invention, 4-aminobutyric acid is prepared using a microorganism as a whole cell, and preferably, 4-aminobutyric acid which has not undergone a complicated refining process such as a crystallization process is directly used to prepare 2-pyrrolidone at a high yield rate in an economically advantageous manner.

(c) According to the present invention, 2-pyrrolidone may be mass-produced at a high yield rate and low production costs.

(d) According to the present invention, without the utility of high temperature/high pressure, 2-pyrrolidone may be obtained from 4-aminobutyric acid with a high purity and a high yield.

(e) The method of the present invention simplifies processes for preparing 2-pyrrolidone, whereby it is suitable for mass production in an industrial scale.

BEST MODE FOR CARRYING OUT THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Throughout the present specification, unless otherwise stated, "%" is used to indicate the concentration of a particular substance, solid/solid is (weight/weight) %, solid/liquid is (weight/volume) % and liquid/liquid is (volume/volume) %.

Example 1

Production of Gamma-Aminobutyric Acid from Glutamic Acid or Glutamate

Figure 1:
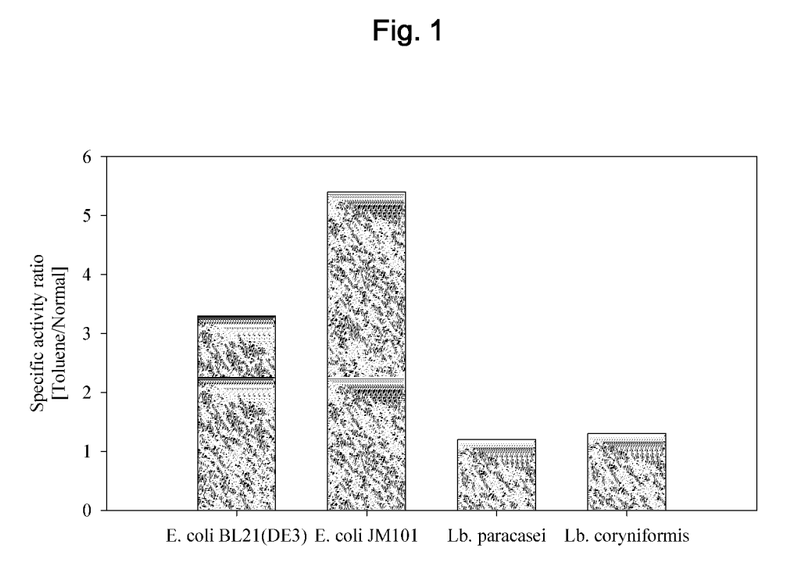
FIG. 1 represents the comparison for the production rate (i.e., specific activity ratio) of gamma-aminobutyric acid in *E. coli* and *Lactobacillus* depending on treatment of the organic solvent.

1-1. Production of Gamma-Aminobutyric Acid from Glutamic Acid Using Various Whole-Cell Catalysts Pre-Treated with Organic Solvents The bacteria containing glutamate decarboxylase, *E. coli* BL21 (DE3), *E. coli* JM101, *Lactobacillus paracasei* and *Lactobacillus coryniformis* (KCTC) were cultured, collected and then divided to two groups, an organic solvent-treated group and a control group. For the organic solvent-treated group, the collected bacterial cells were treated with 0.5% (v/v) of toluene, stirred at 30° C. for 10 min at 200 rpm to destroy selective permeability of microorganisms and then suspended in sterile water. The control group was suspended in sterile water without special treatment processes. To each bacteria suspension as prepared above, 40 µM of pyridoxal 5-phosphate (PLP, Sigma Aldrich) and then 33 wt % of glutamic acid (DAESANG CORPORATION) were added, and the production rates of gamma-aminobutyric acid were measured. For comparison, the production rate of the organic solvent-treated group was divided by that of the non-treated group. As a result, it would be understood that the production rate of gamma-aminobutyric acid in the organic solvent (toluene)-treated group was approximately 1.2-5.5 times higher than that of the non-treated group as shown in FIG. 1.

Figure 2:
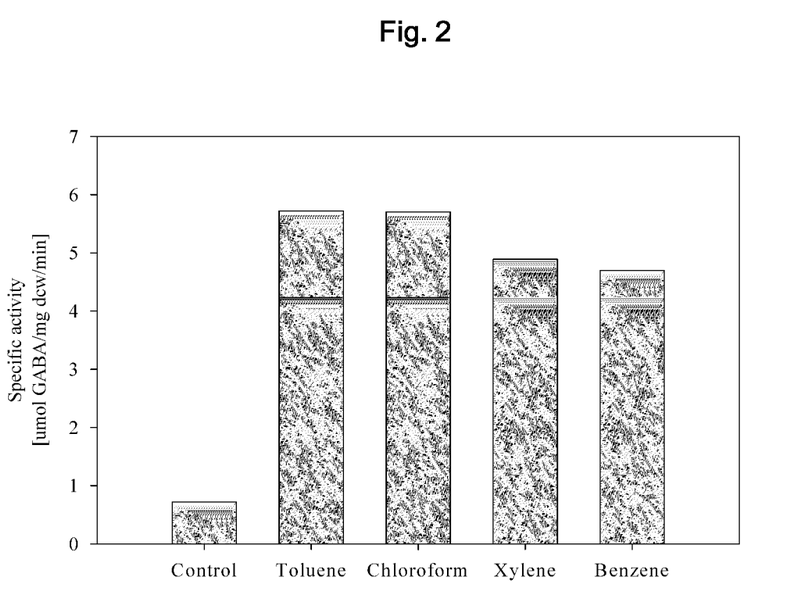
FIG. 2 represents the changes for the production activity (i.e., specific activity) of gamma-aminobutyric acid in microorganisms depending on type of organic solvents.

1-2. Production of Gamma-Aminobutyric Acid from Glutamic Acid in Whole-Cell Catalysts Depending on Organic Solvents The bacteria (*Escherichia coli*) containing glutamate decarboxylase were cultured, collected, treated with organic solvents to destroy selective permeability of microorganisms and then measured production rates of gamma-aminobutyric acid from sodium glutamate (Sigma Aldrich). All organic solvents used herein were hydrophobic organic solvents, toluene, xylene, chloroform, and benzene. The collected bacterial cells were treated with 0.5% (v/v) of the organic solvents, respectively and stirred at 30° C. for 10 min at 200 rpm. To each bacteria suspension as prepared above, 40 µM of pyridoxal 5-phosphate (PLP, Sigma Aldrich) and then 1% (v/v) of sodium glutamate were added, and the production rates of gamma-aminobutyric acid was measured. As a result, the production rate of gamma-aminobutyric acid in the hydrophobic organic solvent-treated group was approximately 5-8 times higher than that of the control group as shown in FIG. 2.

1-3. Increase in GABA Production Activity of Bacteria by Treatment of Organic Solvents The bacteria (*Escherichia coli*) containing glutamate decarboxylase were cultured and collected. The collected bacterial cells were washed with distilled water once and stirred with the organic solvent to destroy selective permeability. At this point, the used organic solvent was toluene which exhibited the fastest production rate of gamma-aminobutyric acid in Example 1-2. The cells were divided to 2 groups, an organic solvent (toluene)-treated group and a control group. The toluene-treated group was treated with 0.5% (v/v) of toluene in bacteria suspension and stirred at 37° C. for 10 min at 150 rpm. After stirring, the bacterial cells were washed with distilled water once. The bacterial cells were suspended in acetate buffer (pH 4.6, 200 mM) and added 0.04 mM of PLP and 1% (v/v) of sodium glutamate to measure production rates of GABA. As a result, the production activity of GABA in the toluene-treated group was 5.72 µmol GABA/mg dcw/min and the production activity of GABA in non-treated group was 0.75 µmol GABA/mg dcw/min.

1-4. Enhancement in Production Activity of GABA Depending on Buffer pH

Figure 3:
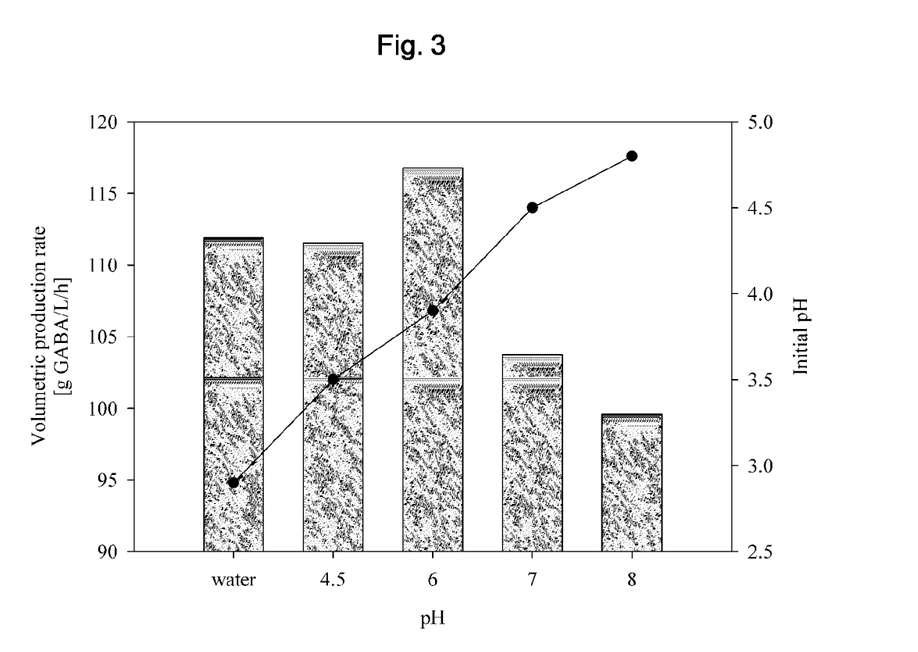
FIG. 3 represents the changes for the volumetric production rate of gamma-aminobutyric acid. The bar graph represents the production rates of gamma-aminobutyric acid, and the line graph represents the initial pH.

The bacteria (*Escherichia coli*) containing glutamate decarboxylase were cultured. The cultured bacterial cells were treated with 0.5% (v/v) of organic solvent toluene as the same manner used in Example 1 and suspended in buffers and sterile water, respectively. Concentrations of all buffers used herein were 100 mM and pH was 4.5, 6.0, 7.0, and 8.0, respectively. The buffer with pH 4.5 was prepared with acetic acid, and the buffers with pH 6.0, 7.0 or 8.0 were prepared with phosphoric acid. To the suspension of the whole-cell catalyst as prepared above, 0.04 mM of PLP and then 10 wt % of sodium glutamate for triggering reaction were added. Afterwards, the initial production rates of GABA were measured to analyze changes in the production rates of GABA depending on buffer pH. As shown in FIG. 3, when the pH 6.0 buffer was used and its initial pH became 3.9, the reaction rate exhibited the maximum reaction rate, 116 g GABA/L/h.

1-5. Production of GABA Using Organic Solvent-Treated Bacterial Cells

The bacteria (*Escherichia coli*) containing glutamate decarboxylase were cultured and collected. The weight of the dried bacterial cells collected was 3.6 g. The bacterial cells were suspended in sterile water, added with 0.5% (v/v) of toluene, stirred at 37° C. for 10 min, centrifuged to collect the bacterial cells and washed with distilled water once. The collected bacterial cells were suspended in 2 L of the buffer (pH 6.0, 100 mM), introduced into a reactor and the resultant was added with 0.04 mM of PLP, 1 kg of sodium glutamate and 50 ppm of polyoxyalkylene glycol to trigger the reaction. The reaction condition was at 30° C. and 200 rpm. The initiate reaction pH was 4.5. The concentration of residual glutamic acid was reduced to less than 1 wt % after only 8 hours and pH was 5.8 at this point. Afterwards, the resultant was treated with a hydrochloric acid solution to decrease to pH 5.5 and further reacted for 1 hour to convert all residual glutamic acid into GABA. The total weight of the produced GABA was 690 g, the mole conversion rate was 98%, and the required time was 9 hours.

Figure 4:
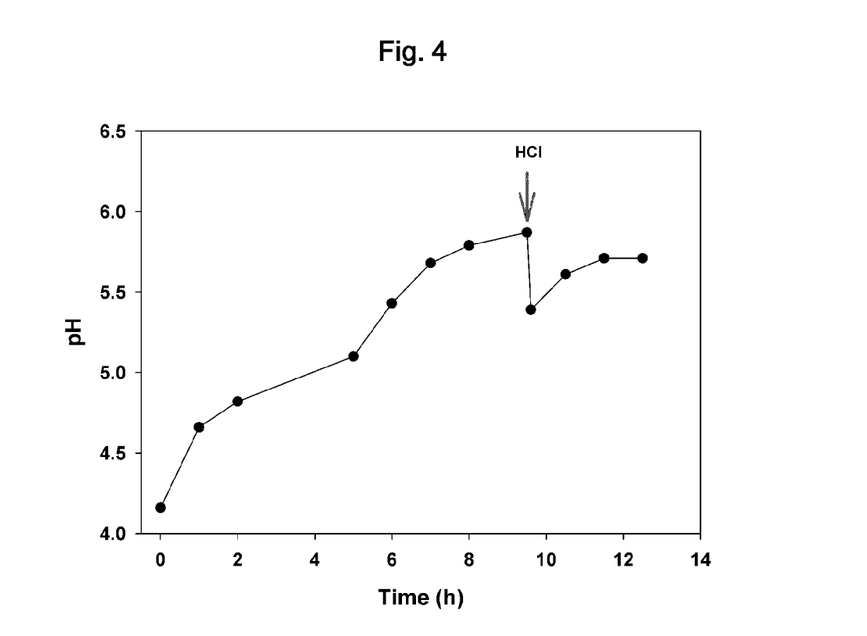
FIG. 4 represents the changes for pH depending on the reaction in GABA production using bacterial cells treated with the organic solvent.

1-6. Production of High-Concentration GABA Using Organic Solvent-Treated Bacterial Cells The bacteria (*Escherichia coli*) containing glutamate decarboxylase were cultured, introduced into a reactor with 0.25% (v/v) of toluene, stirred at 30° C. for 10 min, and centrifuged to collect the bacterial cells. The weight of the dried bacterial cells collected was 50 g. Microorganisms were suspended in buffer or distilled water, introduced into a reactor, and added with 0.04 mM of PLP, 8 kg of sodium glutamate and 500 ppm of polyoxyalkylene glycol to initiate reaction. The reaction condition was at 30° C. and 200 rpm. The reaction conditions were 30° C., 200 rpm and there was no adjustment to any elements, except for above conditions. The initiate reaction pH was 4.0. The concentration of residual glutamic acid was reduced to less than 1 wt % after 10 hours and pH was 5.87 at this point. Afterwards, the resultant was treated with a hydrochloric acid solution to decrease to pH 5.6 and further reacted for 2 hours to convert all residual glutamic acid into GABA (FIG. 4). The concentration of the produced GABA was 34 wt %, mole conversion rate was 98%, and the required time was 12 hours.

1-7. Production of GABA Using Collected Bacterial Cells after Reaction Completion 3.6 g of microorganisms were treated with 0.5% (v/v) of toluene as the same manner used in Example 1-2, and carried out GABA production reaction which use 0.5 kg of glutamic acid as substrate. After 9 hours on the reaction completion, microorganisms were collected by performing centrifugation at 4000 rpm for 10 min. As same manner used in Example 1, the collected microorganisms were washed with distilled water, re-suspended in acetic acid buffer (pH 4.6, 200 mM) and added with 0.04 mM of PLP and 1% (v/v) of sodium glutamate to measure GABA production activity. The GABA production activity value was 4.80 µmol GABA/mg dcw/min. After isolating and collecting for the bacterial cells used in the GABA production reaction, 2 g of the collected bacterial cells was introduced into a reactor containing fresh bacterial cells and was subjected to the reactions as executed in Example 1-2. As a result, the conversion rate was measured to be almost the same as the first reaction and the total reaction time was decreased to 6 hours.

Example 2

Preparation of Gamma-Aminobutyric Acid from Culture Media

The bacterial cells of culture media in Example 1 were removed, heat-treated and decolorized. After isolating bacterial cells by centrifugation, heat treated-culture media were decolorized with activated carbons using stirrer. The culture media were added with 1.0-15.0% of activated carbons (activated carbon weight/gamma-aminobutyric acid weight) to decolorize. After heat treatment, the produced denaturation protein was filtered, isolated with activated carbons, and concentrated to use synthesis of 2-pyrrolidone. As a result, the culture media color showed a tendency to be clear upon increasing the amount of activated carbon. Table 1 represents the recovery efficiency of pyrrolidone synthesis depending on the concentrations of the activated carbon used, where the initial concentration 30.0% of the culture media (gamma-aminobutyric acid weight/culture media volume) was decolorized using activated carbon. Upon increasing concentrations of the activated carbon, the loss rate of GABA was increased such that the recovery efficiency was decreased. In addition, where activated carbon was insufficient, impure pigments were not sufficiently removed such that the recovery efficiency was decreased. Pyrrolidone was synthesized in accordance with the method as described in Example 3-1.

TABLE 1

| | Activated carbon (activated carbon w/GABA w %) | | | | |
|---|---|---|---|---|---|
| | 1 | 2 | 5 | 10 | 15 |
| Recovery efficiency of 2-pyrrolidone synthesis | 90.8 | 94.8 | 92.4 | 90.1 | 90.1 |

It would be understood that the utilization of 2.0% (weight/weight) activated carbon is preferable in order to effectively remove impure pigments in the culture media with minimizing loss of gamma-aminobutyric acid (4-aminobutyric acid).

Example 3

Preparation of 2-Pyrrolidone from Gamma-Aminobutyric Acid

Experimental Example

Analysis for Conversion Efficiency of Gamma-Aminobutyric Acid Depending on Reaction Conditions The present inventors have made various experiments based on the fact that of gamma-aminobutyric acid (4-aminobutyric acid) is converted to 2-pyrrolidone and water at melting temperature, 202° C. As a result, they have found the fact that 4-aminobutyric acid was dissolved at 118-120° C. in the presence of 2-pyrrolidone and the resultant solution was converted to 2-pyrrolidone and water. In addition, where water generated during the reaction was removed under reduced pressure (10-110 mmHg), the reaction time was decreased and the conversion rate for 4-aminobutyric acid to 2-pyrrolidone was increased. They also have found that the higher the reaction temperature, the reaction time becomes shortened (Table 2-4). 4-aminobutyric acid and 2-pyrrolidone were mixed at a weight ratio of 1:1, and reacted at 120° C. (Table 2), 130° C. (Table 3) and 140° C. (Table 4), respectively. The residue amounts (%) of 4-aminobutyric acid under either atmospheric pressure or reduced pressure conditions were hourly measured as summarized in Table 2-4. The residue amounts (%) of 4-aminobutyric acid were analyzed by HPLC (Hewlett Packard 1050 series, Hewlett Packard). There were no side reactions during the reaction. In the reaction solution, 4-aminobutyric acid was reduced and 2-pyrrolidone was increased.

TABLE 2

| Reaction temperature | Reduced pressure condition | Reaction time | | | | |
|---|---|---|---|---|---|---|
| | | 2 hour | 4 hour | 6 hour | 8 hour | 10 hour |
| 120° C. | Atmospheric pressure | 36.3% | 18.4% | 5.2% | 1.5% | 0.9% |
| | Reduced pressure | 29.4% | 6.5% | 1.2% | 0.3% | — |

TABLE 3

| Reaction temperature | Reduced pressure condition | Reaction time (hour) | | | | | | |
|---|---|---|---|---|---|---|---|---|
| | | 1 hour | 2 hour | 3 hour | 4 hour | 5 hour | 6 hour | 7 hour |
| 130° C. | Atmospheric pressure | 35.7% | 25.7% | 17.1% | 11.1% | 5.1% | 2.7% | 2.1% |
| | Reduced pressure | 26.8% | 19.7% | 8.7% | 4.0% | 0.9% | 0.4% | — |

TABLE 4

| Reaction temperature | Reduced pressure condition | Reaction time (hour) | | | | |
|---|---|---|---|---|---|---|
| | | 1 hour | 2 hour | 3 hour | 4 hour | 5 hour |
| 140° C. | Atmospheric pressure | 25.7% | 10.9% | 1.5% | 1.3% | 1.2% |
| | Reduced pressure | 21.1% | 0.7% | 0.3% | — | — |

3-1. Preparation of 2-pyrrolidone from 4-aminobutyric acid (Method 1)

500 g of 2-pyrrolidone (DAESANG CORPORATION) was fed into a 2 L reactor equipped with a cooling distillation device and stirred. To the resultant, 600 g of 4-aminobutyric acid (DAESANG CORPORATION) was added, the temperature was elevated to 135° C.-145° C. under reduced pressure (60-80 mmHg) and stirred, generating 2-pyrrolidone and water by dissolution of 4-aminobutyric acid. Water generated during the reaction was removed under reduced pressure through distillation device. When the reaction mixture becomes transparent, it means the completion of the reaction. With increasing gradually vacuum level, the residual moisture in the reaction solution was removed under reduced pressure (10-20 mmHg). The generated 2-pyrrolidone was distilled under reduced pressure (1-10 mmHg) and collected to obtain 980 g of high purity 2-pyrrolidone as colorless liquid (yield 98.5%, purity 99.5%).

3-2 Preparation of 2-pyrrolidone from 4-aminobutyric acid (Method 2)

1200 g of 4-aminobutyric acid and a 2 L reactor equipped with a cooling distillation device were prepared. First, 200 g of 4-aminobutyric acid was fed into the 2 L reactor. The temperature of the reactor was elevated to the melting temperature of 4-aminobutyric acid (202° C.) and 4-aminobutyric acid was dissolved to generate 2-pyrrolidone and water. The temperature of the reactor was naturally cooled. To this, 200 g of 4-amino butyric acid was added to dissolve. The remaining 800 g of 4-aminobutyric acid was added at 135° C.-145° C. of the reactor temperature to dissolve. Water generated during the reaction was removed under atmospheric pressure or reduced pressure (40-60 mmHg) through distillation device. When the reaction mixture becomes transparent, it means the completion of the reaction. With increasing gradually vacuum level, the residual moisture in the reaction solution was removed under reduced pressure (20-30 mmHg). The generated 2-pyrrolidone was distilled under reduced pressure (1-10 mmHg) and collected to obtain 951 g of high purity 2-pyrrolidone (yield 96%, purity 99.5%) as colorless liquid. Where the generated water was removed at atmospheric pressure, 2-pyrrolidone was obtained with same values of the yield and purity described above. However, the reaction time is 2 hours longer than the reaction time of the reduced pressure condition.

3-3. Preparation of 2-pyrrolidone from 4-aminobutyric acid (Method 3)

1200 g of 4-aminobutyric acid was fed into a 2 L reactor equipped with a cooling distillation device under the stirrer stopped. The temperature of the reactor was elevated to 200° C.-210° C. and 4-aminobutyric acid was partially dissolved to generate 2-pyrrolidone and water. If possible, stirring agitator was slowly begun to stir. The reactor was naturally cooled with stirring, and the remaining of 4-aminobutyric acid was dissolved at 135° C.-145° C. of the reactor temperature. Water generated during the reaction was removed under atmospheric pressure or reduced pressure (40-60 mmHg) through distillation device. When the reaction mixture becomes transparent, it means the completion of the reaction. With increasing gradually vacuum level, the residual moisture in the reaction solution was removed under reduced pressure (20-30 mmHg). The generated 2-pyrrolidone was distilled under reduced pressure (1-10 mmHg) and collected to obtain 960 g of high purity 2-pyrrolidone (yield 96.9%, purity 99.5%) as colorless liquid. Where the generated water was removed at atmospheric pressure, 2-pyrrolidone was obtained with same values of the yield and purity described above. However, the reaction time is 2 hours longer than the reaction time of the reduced pressure condition.

3-4. Preparation of 2-pyrrolidone from 4-aminobutyric acid 500 g of 2-pyrrolidone was fed into a 2 L reactor equipped with a cooling distillation device and stirred. To the resultant, 600 g of 4-aminobutyric acid was added, the temperature was elevated to 118° C.-120° C. and stirred for approximately 10 hours. Samples of the reaction solution were collected to verify the residual concentration of 4-aminobutyric acid 0.9% by analyzing using HPLC, and then the reaction was stopped. Water generated after the reaction was removed under 20-30 mmHg through distillation device. The remaining 2-pyrrolidone in the reactor was distilled under reduced pressure (1-10 mmHg) and collected to obtain 974 g of high purity 2-pyrrolidone (yield 97.9%, purity 99.4%) as colorless liquid.

3-5 Preparation of 2-pyrrolidone from 4-aminobutyric acid 500 g of 2-pyrrolidone was fed into a 2 L reactor equipped with a cooling distillation device and stirred. To the resultant, 600 g of 4-aminobutyric acid was added, the temperature was elevated to 118° C.-120° C. under reduced pressure (20-30 mmHg) and stirred, generating 2-pyrrolidone and water by dissolution of 4-aminobutyric acid. Water generated was removed through distillation device. After approximately 8 hours reaction, samples of the reaction solution were collected to verify residual concentration of 4-aminobutyric acid 0.3% by analyzing using HPLC, and then the reaction was stopped. With increasing gradually vacuum level, the residual moisture in the reaction solution was completely removed. The remaining 2-pyrrolidone in the reactor was distilled under reduced pressure (1-10 mmHg) and collected to obtain 985 g of high purity 2-pyrrolidone (yield 99%, purity 99.8%) as colorless liquid.

3-6. Preparation of 2-pyrrolidone from 4-aminobutyric acid 500 g of 2-pyrrolidone was fed into a 2 L reactor equipped with a cooling distillation device and stirred. To the resultant, 600 g of 4-aminobutyric acid was added, the temperature was elevated to 128° C.-132° C. under reduced pressure (30-50 mmHg) and stirred, generating 2-pyrrolidone and water by dissolution of 4-aminobutyric acid. Water generated was removed under reduced pressure through distillation device. After approximately 8 hours reaction, samples of the reaction solution were collected to verify residual concentration of 4-aminobutyric acid 0.4% by analyzing using HPLC, and then the reaction was stopped. With increasing gradually vacuum level, the residual moisture in the reaction solution was completely removed. The remaining 2-pyrrolidone in the reactor was distilled under reduced pressure (1-10 mmHg) and collected to obtain 980 g of high purity 2-pyrrolidone (yield 98.5%, purity 99.6%) as colorless liquid.

3-7. Preparation of 2-pyrrolidone from 4-aminobutyric acid 500 g of 2-pyrrolidone was fed into a 2 L reactor equipped with a cooling distillation device and stirred. To the resultant, 600 g of 4-aminobutyric acid was added, the temperature was elevated to 138° C.-142° C. under reduced pressure (60-80 mmHg) and stirred, generating 2-pyrrolidone and water by dissolution of 4-aminobutyric acid. Water generated was removed under reduced pressure through distillation device. After approximately 3 hours reaction, samples of the reaction solution were collected to verify residual concentration of 4-aminobutyric acid 0.3% by analyzing using HPLC, and then the reaction was stopped. With increasing gradually vacuum level, the residual moisture in the reaction solution was completely removed. The remaining 2-pyrrolidone in the reactor was distilled under reduced pressure (1-10 mmHg) and collected to obtain 985 g of high purity 2-pyrrolidone (yield 99%, purity 99.1%) as colorless liquid.

3-8. Preparation of 2-pyrrolidone from 4-aminobutyric acid 500 g of 2-pyrrolidone was fed into a 2 L reactor attached cooling distillation device and stirred. To the resultant, 600 g of 4-aminobutyric acid was added, the temperature was elevated to 145° C.-148° C. under reduced pressure (70-110 mmHg) and stirred, generating 2-pyrrolidone and water by dissolution of 4-aminobutyric acid. Water generated was removed under reduced pressure through distillation device. After approximately 2 hours reaction, samples of the reaction solution were collected to verify residual concentration of 4-aminobutyric acid 0.3% by analyzing using HPLC, and then the reaction was stopped. With increasing gradually vacuum level, the residual moisture in the reaction solution was completely removed. The remaining 2-pyrrolidone in the reactor was distilled under reduced pressure (1-10 mmHg) and collected to obtain 978 g of high purity 2-pyrrolidone (yield 98.3%, purity 99.3%) as colorless liquid.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for preparing 2-pyrrolidone, comprising the steps of:
    (a) preparing 4-aminobutyric acid by culturing a microorganism as a whole-cell catalyst which contains glutamate decarboxylase in a culture medium containing glutamic acid or glutamate;
    (b) obtaining 4-aminobutyric acid by filtering the culture medium; and
    (c) converting 4-aminobutyric acid to 2-pyrrolidone.

2. The method according to claim 1, wherein the microorganism is pre-treated with a hydrophobic organic solvent.

3. The method according to claim 1, wherein the microorganism containing glutamate decarboxylase in the step (a) is *Escherichia coli*.

4. The method according to claim 2, wherein the hydrophobic organic solvent is selected from the group consisting of toluene, chloroform, xylene, benzene and cyclohexane.

5. The method according to claim 1, wherein the step (a) is performed in a buffering region, pH 3.0-8.0.

6. The method according to claim 1, wherein, between the steps (a) and (b), the method further comprises the step of removing a pigment in the culture media by treating the culture media with an activated carbon.

7. The method according to claim 6, wherein the activated carbon is added in the amount of 1.5-4.0 wt % based on the weight of 4-aminobutyric acid in the culture media.

8. The method according to claim 1, wherein, after the step (b), the method further comprises the step of isolating the whole-cell catalyst and reusing the isolated whole-cell catalyst.

9. The method according to claim 1, wherein the 4-aminobutyric acid of step (c) is non-pre-purified.

10. The method according to claim 1, wherein the step (c) comprises the substeps of:
    (c-1) preparing a reaction composition in which 4-aminobutyric acid and 2-pyrrolidone are mixed;
    (c-2) generating 2-pyrrolidone and water by heating the reaction composition for lactam cyclization reaction; and
    (c-3) isolating 2-pyrrolidone.

11. The method according to claim 10, wherein the step (c) is performed under a reduced pressure condition.

12. The method according to claim 11, wherein the reduced pressure is below 100 mmHg.

13. The method according to claim 12, wherein the reduced pressure is 10-50 mmHg.

14. The method according to claim 11, wherein the step (c-2) is performed at 110° C.-150° C.

15. The method according to claim 10, wherein the step (c-2) is performed at 118° C.-148° C.

16. The method according to claim 15, wherein the step (c) is performed by distillation under reduced pressure.

17. The method according to claim 1, wherein the method shows a maximum yield of 99% and a maximum purity of 99.8% for 2-pyrrolidone.

* * * * *